(12) United States Patent
Wulfman et al.

(10) Patent No.: US 11,597,164 B2
(45) Date of Patent: Mar. 7, 2023

(54) FIBROUS JOINERY INTERFACE BETWEEN STRUCTURES

(71) Applicant: Cardiac Pacemakers, Inc., St Paul, MN (US)

(72) Inventors: David Robert Wulfman, Minneapolis, MN (US); Joel T. Eggert, Plymouth, MN (US); Diana K. Ma, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1003 days.

(21) Appl. No.: 16/377,630

(22) Filed: Apr. 8, 2019

(65) Prior Publication Data

US 2019/0232573 A1 Aug. 1, 2019

Related U.S. Application Data

(62) Division of application No. 14/972,726, filed on Dec. 17, 2015, now abandoned.

(Continued)

(51) Int. Cl.
*B29C 65/00* (2006.01)
*A61N 1/05* (2006.01)
(Continued)

(52) U.S. Cl.
CPC .............. *B29C 66/712* (2013.01); *A61N 1/05* (2013.01); *B29B 11/10* (2013.01); *B29C 65/02* (2013.01);
(Continued)

(58) Field of Classification Search
CPC . B29C 66/712; B29C 66/612; B29C 66/5221; B29C 66/3034; B29C 66/1224;
(Continued)

(56) References Cited

U.S. PATENT DOCUMENTS 6,656,318 B1 12/2003 Sabouraud et al.
7,218,972 B2 5/2007 Rodriguez
(Continued)

FOREIGN PATENT DOCUMENTS

CN 102258805 A 11/2011
CN 103170013 A 6/2013
(Continued)

OTHER PUBLICATIONS

International Search Report and Written Opinion issued in PCT/US2015/066380, dated Mar. 14, 2016, 13 pages.

*Primary Examiner* — Daniel McNally
(74) *Attorney, Agent, or Firm* — Nelson Mullins Riley & Scarborough LLP

(57) ABSTRACT

An implantable medical device includes a first component including a first material, a second component including a second material, and a fiber matrix including a plurality of fibers. The fiber matrix joins the first component to the second component. The fiber matrix includes a first a first portion connected to the first component, and a second portion connected to the second component. The first portion of the fiber matrix is interpenetrated with, and mechanically fixed to, the first material. The first portion of the fiber matrix directly contacts the first material.

20 Claims, 4 Drawing Sheets

Related U.S. Application Data

(60) Provisional application No. 62/093,872, filed on Dec. 18, 2014.

(51) Int. Cl.

| | | |
|---|---|---|
| *B32B 27/28* | (2006.01) | |
| *B32B 27/40* | (2006.01) | |
| *B32B 7/04* | (2019.01) | |
| *B32B 7/12* | (2006.01) | |
| *B32B 27/08* | (2006.01) | |
| *D01D 5/00* | (2006.01) | |
| *B29B 11/10* | (2006.01) | |
| *B29C 65/02* | (2006.01) | |
| *B29C 70/42* | (2006.01) | |
| *A61M 25/00* | (2006.01) | |
| *B29C 65/48* | (2006.01) | |
| *B29K 75/00* | (2006.01) | |
| *B29K 83/00* | (2006.01) | |
| *B29L 23/00* | (2006.01) | |

(52) U.S. Cl.
CPC ...... *B29C 66/1222* (2013.01); *B29C 66/1224* (2013.01); *B29C 66/3034* (2013.01); *B29C 66/5221* (2013.01); *B29C 66/612* (2013.01); *B29C 70/42* (2013.01); *B32B 7/04* (2013.01); *B32B 7/12* (2013.01); *B32B 27/08* (2013.01); *B32B 27/283* (2013.01); *B32B 27/285* (2013.01); *B32B 27/288* (2013.01); *B32B 27/40* (2013.01); *D01D 5/0007* (2013.01); *A61B 2562/12* (2013.01); *A61M 25/0009* (2013.01); *B29C 65/4895* (2013.01); *B29C 66/71* (2013.01); *B29C 66/7392* (2013.01); *B29C 66/7394* (2013.01); *B29K 2075/00* (2013.01); *B29K 2083/00* (2013.01); *B29L 2023/007* (2013.01); *B32B 2255/10* (2013.01); *B32B 2255/26* (2013.01); *B32B 2262/00* (2013.01); *B32B 2535/00* (2013.01); *B32B 2597/00* (2013.01)

(58) Field of Classification Search
CPC ..... B29C 66/1222; B29C 65/02; B29C 70/42; D01D 5/0007

See application file for complete search history.

(56) References Cited

U.S. PATENT DOCUMENTS

| | | | |
|---|---|---|---|
| 7,955,644 | B2 | 6/2011 | Sansom et al. |
| 8,229,569 | B1 | 7/2012 | Palma et al. |
| 8,688,232 | B2 | 4/2014 | Finley et al. |
| 9,415,206 | B2 | 8/2016 | Arnholt et al. |
| 2002/0173785 | A1 | 11/2002 | Spear et al. |
| 2003/0105453 | A1 | 6/2003 | Stewart et al. |
| 2004/0067705 | A1* | 4/2004 | Ton-That ............... B32B 27/08 442/65 |
| 2004/0199234 | A1 | 10/2004 | Rodriguez |
| 2008/0145616 | A1* | 6/2008 | Gharib ................... B82Y 30/00 156/298 |
| 2010/0206803 | A1 | 8/2010 | Ward et al. |
| 2010/0217257 | A1 | 8/2010 | Howat et al. |
| 2011/0054581 | A1 | 3/2011 | Desai et al. |
| 2011/0184513 | A1 | 7/2011 | Myung et al. |
| 2012/0330355 | A1 | 12/2012 | Finley et al. |
| 2013/0041442 | A1 | 2/2013 | Arnholt et al. |
| 2013/0268062 | A1 | 10/2013 | Puckett et al. |
| 2014/0074201 | A1 | 3/2014 | Arnholt et al. |
| 2014/0141256 | A1 | 5/2014 | Padsalgikar |
| 2014/0343549 | A1 | 11/2014 | Spear et al. |
| 2015/0025608 | A1* | 1/2015 | Delaney, Jr. .......... A61N 1/056 607/116 |
| 2015/0343200 | A1 | 12/2015 | Arnholt et al. |
| 2016/0176107 | A1 | 6/2016 | Wulfman et al. |

FOREIGN PATENT DOCUMENTS

| | | |
|---|---|---|
| JP | 2005-523126 A | 8/2005 |
| JP | 2014-525279 A | 9/2014 |

\* cited by examiner

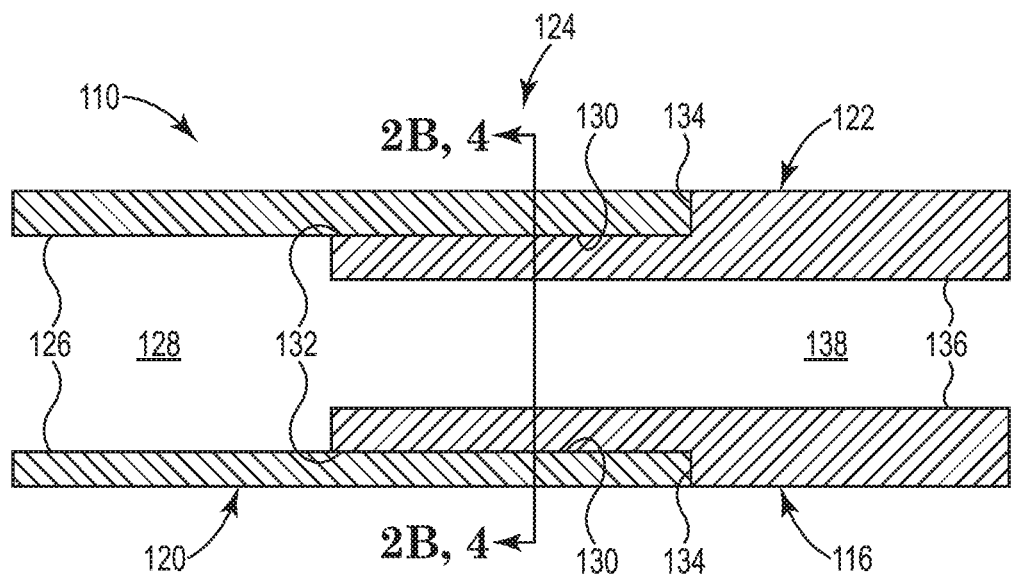
Fig. 2A
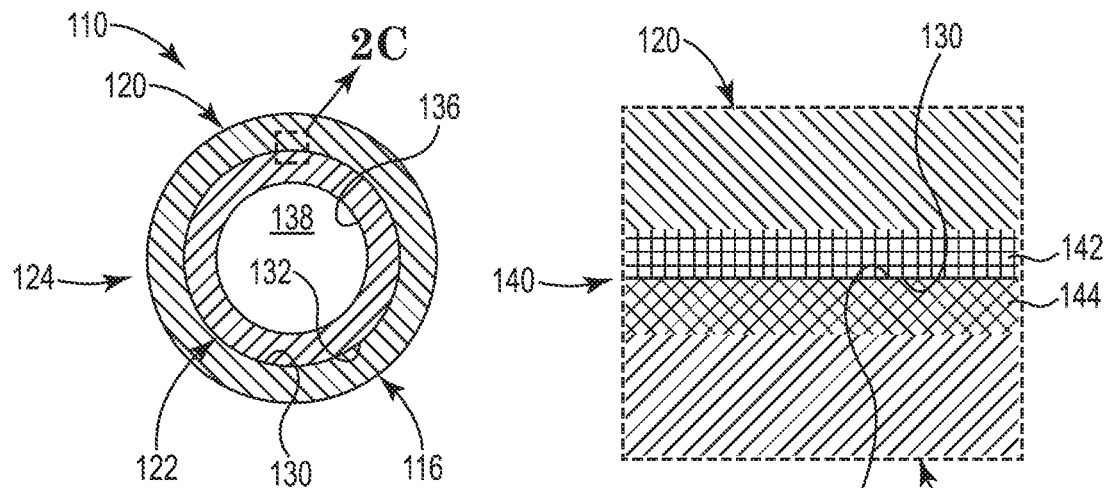
Fig. 2B
Fig. 2C

FIBROUS JOINERY INTERFACE BETWEEN STRUCTURES

CROSS-REFERENCE TO RELATED APPLICATION

This application is a division of U.S. application Ser. No. 14/972,726, filed Dec. 17, 2015, which claims priority under 35 U.S.C. § 119 to U.S. Provisional Application No. 62/093,872, filed Dec. 18, 2014, which is herein incorporated by reference in its entirety.

TECHNICAL FIELD

The present invention relates to a structure for joining materials that are not readily bondable to each other. More specifically, the invention relates to structures and methods for joining components of a medical device that are not readily bondable to each other.

BACKGROUND

Medical devices, particularly implantable medical devices, often consist of a variety of materials having physical characteristics beneficial for a specific application. For example, implantable medical leads may be formed from a biocompatible polyurethane polymer, such as a thermoplastic polycarbonate polyurethane. In some embodiments, it may be desirable to attach an external non-polyurethane polymer, such as a silicone polymer, component to at least a portion of an implantable medical lead. For example, creating a joint that attaches a silicone polymer to a polyurethane polymer may require a series of complex processing operations, for example preparing the polyurethane polymer and/or silicone polymer surfaces, because silicone polymer and polyurethane polymer are typically not readily bondable to each other. In some embodiments, such processing may include plasma treating a polyurethane polymer surface to clean and/or chemically activate the surface. The process may additionally or alternatively include applying a primer or adhesive to the polyurethane polymer surface before applying, such as overmolding, the silicone polymer onto the prepared polyurethane polymer surface. Often such complex processing must be completed in a short span of time because the polyurethane polymer surface may begin to deteriorate after it is prepared. If the polyurethane polymer surface deteriorates to a certain extent, the joint that forms between the silicone polymer and the polyurethane polymer may not have adequate strength.

Other material combinations in which the materials are not readily bondable to each other may require similarly complex processing. Example material combinations include silicone polymer and polyether ether ketone. Additionally many thermoplastics cannot be readily heat bonded to thermoset polymers, and require additional processing. Joining materials which are not readily bondable to each other may require surface treatment and/or adhesives which may take significant time to cure, thus slowing production of the medical devices and increasing their cost. What is needed is a better method for joining materials that are not readily bondable to each other.

SUMMARY

In Example 1, an implantable medical device includes a first component including a first material, a second component including a second material, and a fiber matrix including a plurality of fibers, the fiber matrix joining the first component to the second component. The fiber matrix includes a first portion of the fiber matrix connected to the first component; and a second portion of the fiber matrix connected to the second component. The first portion of the fiber matrix is interpenetrated with, and mechanically fixed to, the first material. The first portion of the fiber matrix directly contacts the first material.

In Example 2, the device of Example 1, wherein the first material is a silicone polymer, the second material is a polyurethane polymer, and the fiber matrix is a polyurethane polymer.

In Example 3, the device of any of Examples 1-2, wherein at least some of the plurality of fibers in the second portion of the fiber matrix are distinctly identifiable within the second component.

In Example 4, the device of any of Examples 1-3, wherein the second portion of the fiber matrix is bonded to the second component by a heat bond.

In Example 5, the device of any of Examples 1-3, wherein the second portion of the fiber matrix is interpenetrated with, and mechanically fixed to, the second material, and wherein the second portion of the fiber matrix directly contacts the second material.

In Example 6, the device of Example 5, wherein the first material is a silicone polymer, the second material is a polyurethane polymer, and the fiber matrix is an aliphatic polyamide polymer.

In Example 7, the device of any of Examples 1-6, wherein each fiber of the plurality of fibers has a diameter between 0.1 micrometers and 2 micrometers.

In Example 8, the device of any of Examples 1-7, wherein at least some of the plurality of fibers include a single fiber extending a plurality of times between the first component and the second component.

In Example 9, a method for joining a first component and a second component of an implantable medical device includes: interpenetrating a first portion of a fiber matrix within a first material, the first material being in a liquid state; forming the first component by solidifying the first material, wherein the first portion of the fiber matrix is mechanically fixed within a portion of the first component and a second portion of the fiber matrix projects from the first component; and connecting the second portion of the fiber matrix to the second component to join the first component to the second component.

In Example 10, the method of Example 9, wherein interpenetrating the first portion of the fiber matrix within the first material includes electro-spinning a fiber directly into the first material.

In Example 11, the method of Example 9, wherein interpenetrating the first portion of the fiber matrix within the first material includes electro-spinning a plurality of fibers onto a substrate to form the fiber matrix, and overmolding the first material onto the fiber matrix on the substrate.

In Example 12, the method of any of Examples 9-11, wherein solidifying the first material is by cross-linking portions of the first material around portions of the first portion of the fiber matrix.

In Example 13, the method of any of Examples 9-12, wherein connecting the second portion of the fiber matrix to the second component includes heat bonding the second portion of the fiber matrix to the second component.

In Example 14, the method of any of Examples 9-12, wherein connecting the second portion of the fiber matrix to the second component includes interpenetrating the second portion of the fiber matrix within a liquid solution including a first portion of the second material, solidifying the first portion of the second material evaporating a solvent from the liquid solution such that the second portion of the fiber matrix is mechanically fixed within the first portion of the second component, and forming the second component by heat bonding a second portion of the second component to the first portion of the second component such that at least a portion of the second portion of the fiber matrix is distinctly identifiable within the second component.

In Example 15, the method of Example 14, wherein the first material is a silicone polymer, the second material is a polyurethane polymer, and the fiber matrix is an aliphatic polyamide polymer.

In Example 16, a joint structure between two components of an implantable medical device includes: a first component made of a first material; a second component made of a second material; and a fiber matrix including a plurality of fibers. The fiber matrix joins the first component to the second component. The fiber matrix includes a first portion of the fiber matrix connected to the first component, and a second portion of the fiber matrix connected to the second component. The first portion of the fiber matrix is interpenetrated with, and mechanically fixed to, the first material. The first portion of the fiber matrix directly contacts the first material.

In Example 17, the joint structure of Example 16, wherein the first material is a silicone polymer, the second material is a polyurethane polymer, and the fiber matrix is a polyurethane polymer.

In Example 18, the joint structure of and of Examples 16-17, wherein at least some of the plurality of fibers in the second portion of the fiber matrix are distinctly identifiable within the second component.

In Example 19, the joint structure of any of Examples 16-18, wherein the second portion of the fiber matrix is connected to the second component by a heat bond.

In Example 20, the joint structure of Example 16, wherein the second portion of the fiber matrix is interpenetrated with, and mechanically fixed to, the second material, and wherein the second portion of the fiber matrix directly contacts the second material.

In Example 21, the joint structure of Example 20, wherein the first material is a silicone polymer, the second material is a polyurethane polymer, and the fiber matrix is an aliphatic polyamide polymer.

In Example 22, the joint structure of any of Examples 16-21, wherein each fiber of the plurality of fibers has a diameter between 0.1 micrometers and 2 micrometers.

In Example 23, the joint structure of any of Examples 16-22, wherein at least some of the plurality of fibers are randomly oriented.

In Example 24, the joint structure of Example 16-23, wherein at least some of the plurality of fibers include a single fiber extending a plurality of times between the first component and the second component.

In Example 25, a method for joining a first component and a second component of an implantable medical device includes: interpenetrating a first portion of a fiber matrix within a first material, the first material being in a liquid state; forming the first component by solidifying the first material, wherein the first portion of the fiber matrix is mechanically fixed within a portion of the first component and a second portion of the fiber matrix projects from the first component; and connecting the second portion of the fiber matrix to the second component to join the first component to the second component.

In Example 26, the method of Example 25, wherein interpenetrating the first portion of the fiber matrix within the first material includes electro-spinning a fiber directly into the first material.

In Example 27, the method of Example 25, wherein interpenetrating the first portion of the fiber matrix within the first material includes electro-spinning at least one fiber onto a substrate to form the fiber matrix, and overmolding the first material onto the fiber matrix on the substrate.

In Example 28, the method of any of Examples 25-27, wherein solidifying the first material is by cross-linking portions of the first material around portions of the first portion of the fiber matrix.

In Example 29, the method of any of Examples 25-28, wherein connecting the second portion of the fiber matrix to the second component includes heat bonding the second portion of the fiber matrix to the second component.

In Example 30, the method of any of Examples 25-28, wherein connecting the second portion of the fiber matrix to the second component includes: interpenetrating the second portion of the fiber matrix within a liquid solution including a first portion of the second material; solidifying the first portion of the second material evaporating a solvent from the liquid solution such that the second portion of the fiber matrix is mechanically fixed within the first portion of the second component; and forming the second component by heat bonding a second portion of the second component to the first portion of the second component such that at least a portion of the second portion of the fiber matrix is distinctly identifiable within the second component.

In Example 31, the method of Example 30, wherein the first material is a silicone polymer, the second material is a polyurethane polymer, and the fiber matrix is an aliphatic polyamide polymer.

In Example 32, an implantable medical device includes a first tubular structure, a second tubular structure coaxial with the first tubular structure, and a fiber matrix joining the first tubular structure to the second tubular structure. The fiber matrix includes: a first portion of the fiber matrix interpenetrated within, and mechanically fixed to, the first tubular structure; and a second portion of the fiber matrix connected to the second tubular structure. The first portion of the fiber matrix directly contacts the first tubular structure.

In Example 33, the device of Example 32, wherein the second tubular structure is at least partially within the first tubular structure.

In Example 34, the device of any of Examples 32-33, wherein the first tubular structure is made of a silicone polymer, the second tubular structure is made of a polyurethane polymer, and the fiber matrix is made of a polyurethane polymer.

In Example 35, the device of any of Examples 32-33, wherein the first tubular structure is a silicone polymer, the second tubular structure is a polyurethane polymer, and the fiber matrix is an aliphatic polyamide polymer; and wherein the second portion of the fiber matrix is interpenetrated with, and mechanically fixed to, the second tubular structure, and wherein the second portion of the fiber matrix directly contacts the second tubular structure.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 2A-2C are schematic views of a portion of the implantable medical device shown FIG. 1.

Figure 1:
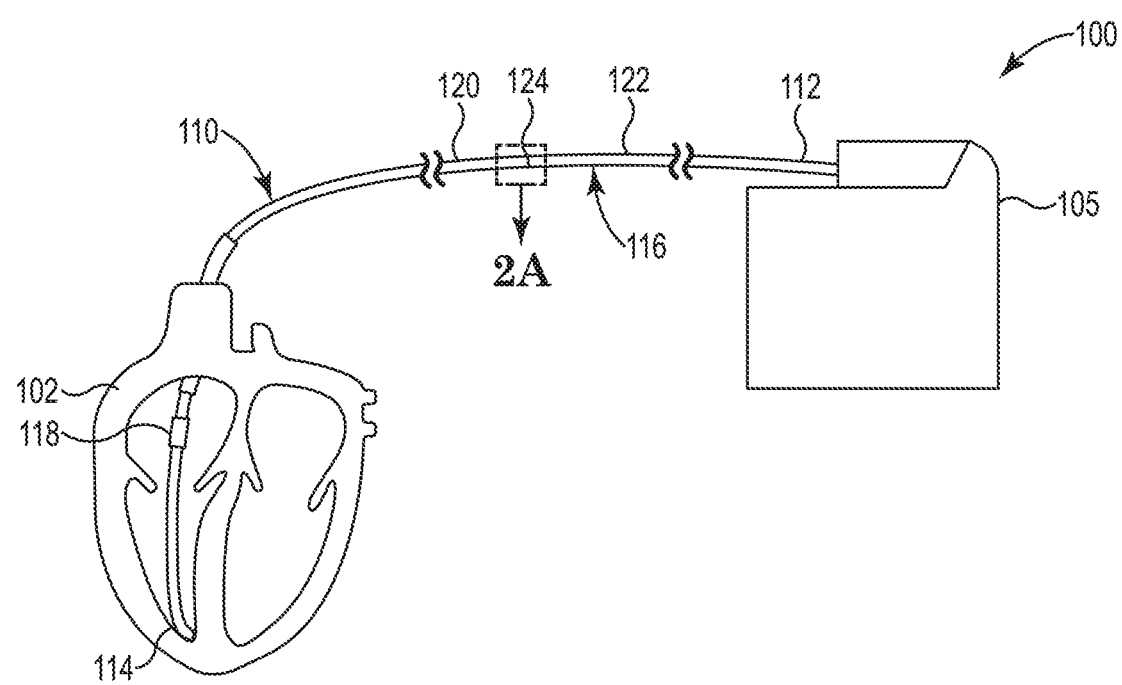
FIG. 1 illustrates an exemplary implantable medical device.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

In accordance with various aspects of the disclosure, an implantable medical device can be an implantable medical electrical device, such as a medical electrical lead discussed below.

FIG. 1 is a schematic illustration of a lead system 100 for delivering and/or receiving electrical pulses or signals to stimulate, shock, and/or sense a heart 102. The lead system 100 includes a pulse generator 105 and a medical electrical lead 110. The pulse generator 105 includes a source of power as well as an electronic circuitry portion. The pulse generator 105 may be a battery-powered device which generates a series of timed electrical discharges or pulses. The pulse generator 105 is generally implanted into a subcutaneous pocket made in the wall of the chest. Alternatively, the pulse generator 105 may be placed in a subcutaneous pocket made in the abdomen, or in another location. It should be noted that while the medical electrical lead 110 is illustrated for use with a heart 102, the medical electrical lead 110 is suitable for other forms of electrical stimulation/sensing as well.

In some embodiments, the medical electrical lead 110 extends from a proximal end 112, where it is coupled with the pulse generator 105 to a distal end 114, which is coupled with a portion of the heart 102, when implanted or otherwise coupled therewith. The medical lead 110 includes a lead body 116 extending generally from the proximal end 112 to the distal end 114. The lead body 116 may be a tubular structure. Disposed along a portion of the medical electrical lead 110, for example near the distal end, may be at least one electrode 118 which electrically couples the medical electrical lead 110 with the heart 102. At least one electrical conductor (not shown) may be disposed within the lead body 116 and extend generally from the proximal end 112 to the distal end 114. The at least one electrical conductor electrically couples the electrode 118 with the proximal end 112 of the medical electrical lead 110. The electrical conductor carries electrical current and pulses between the pulse generator 105 and the electrode 118, and to and from the heart 102.

In some embodiments, lead body 116 may include a first component 120 made of a first material and a second component 122 made of a second material. The first component 120 may extend from the distal end 114, and the second component 122 may extend from the proximal end 114. The first component 120 and the second component 122 may be connected at a lead body transition 124 to form the lead body 116. In some embodiments, the second material may be different from the first material to imbue different portions of lead body 116 with different beneficial physical characteristics. For example, in some embodiments, the first material may be a very flexible and easily compliant material, such as silicone, to permit the first component 120, a portion of which may be adjacent to or within the heart 102, to easily conform to changes in the shape of the heart 102 as it beats. In contrast, in some embodiments, the second material may be a less flexible, less compliant material, such as polyurethane, to provide the second component 122 with the stiffness necessary to accurately control the positioning of the lead body 116. In some embodiments, the first material and the second material may not be readily bondable to one another. Two materials may be considered readily bondable if the materials can be directly joined to each other without the use of a surface treatment (other than surface cleaning) or an intervening third material such as, for example, an adhesion promoter or an adhesive. This presents a challenge in embodiments in which it is desired that the first component 120 be securely connected to the second component 122 at lead body transition 124 to form lead body 116. Embodiments described below employ a fiber matrix to securely connect or attach two components made of materials that do not readily bond to each other. Although the embodiments below illustrate connecting together components of a lead body, it is understood that the present invention is suitable for a connection between any two surfaces of an implantable medical device.

FIGS. 2A-2C are schematic views of a portion of the implantable medical electrical lead 110 shown in FIG. 1. FIGS. 2A and 2B are, respectively, longitudinal and axial cross-sectional views of a portion of the medical electrical lead 110 showing a portion of the lead body 116 including the lead body transition 124 connecting the first component 120 to the second component 122. As shown in FIG. 2A, in some embodiments the first component 120 may include a first inner lead surface 126, a first lumen 128, and a first transition surface 130. The first lumen 128 may be defined by the first inner lead surface 126, and may extend generally from any location along the first component 120 to the lead body transition 124. As shown in FIG. 2A, in some embodiments, the second component 122 may include a second transition surface 132, a transition stop 134, a second inner lead surface 136, and a second lumen 138. The second lumen 138 may be defined by the second inner lead surface 136, and may extend generally from any location along the second component 122 through the lead body transition 124. Together, the first lumen 128 and the second lumen 138 form a lumen that may run the length of, and along the axis lead body 116, and overlap at the lead body transition 124.

As shown in FIGS. 2A and 2B together, in some embodiments, the second transition surface 132 is a radially outward facing surface of the second component 122 that may be at an end of the second component 122 opposite the proximal end 112 (FIG. 1), and may be recessed radially from an outer surface of lead body 116 at the transition stop 134. In some embodiments, the first transition surface 130 is a portion of the first inner lead surface 126 that may be at an end of the first component 120 opposite the distal end 114

(FIG. 1). As shown in FIG. 2A, in some embodiments, an end of the first component 120 butts up against the transition stop 134 and the lead body transition 124 extends from the transition stop 134 to an end of the second transition surface 132 opposite the transition stop 134.

As shown in FIGS. 2A and 2B, in some embodiments, the second transition surface 132 may be adjacent to, and may be in contact with, the first inner lead surface 126 at the first transition surface 130. In some embodiments, the first component 120 and the second component 122 may be physically joined at first transition surface 130 and second transition surface 132, forming lead body transition 124. In some embodiments, the joint structure between the first transition surface 130 and the second transition surface 132 securely connects the first component 120 to the second component 122.

FIG. 2C is a schematic enhanced view showing a portion of the joint structure connecting the first component 120 to the second component 122, according to some embodiments. As shown in FIG. 2C, the joint structure may include a fiber matrix 140, including a first portion 142 and a second portion 144. The fiber matrix 140 may include a plurality of fibers and spaces between fibers, as described below. As shown in FIG. 2C, the first portion 142 may be connected to the first component 120 at the first transition surface 130. The first portion 142 may be interpenetrated with the first component 120. That is, the first material of the first component 120 may be intermingled with, and fill at least some of the spaces between, fibers in the first portion 142 of the fiber matrix 140. Thus, the first portion 142 may be mechanically fixed to the first component 120 without a need for a third material, such as but not limited to an adhesive and/or primer, between the first component 120 and the second component 122. Because the first portion 142 may be mechanically fixed to the first component 120, the fiber matrix 140 may be made of a material that does not bond readily to the first material of the first component 120. In some embodiments, the first portion 142 directly contacts the first material of the first component 120, as there is no need for a third material between the first portion 142 and the first component 120.

As further shown in FIG. 2C, the second portion 144 of the fiber matrix 140 may connect to the second component 122 at the second transition surface 132. In some embodiments, the fiber matrix 140 may be made of a material that bonds readily to the second material. In other embodiments, the fiber matrix 140 may be made of the second material. In such embodiments, the second portion 144 may be readily bonded to the second component 122 at the second transition surface 132 by, for example, heat bonding. A heat bond may be formed when a material, such as the second material, is heated enough to soften the material, but not completely melt the material. In some embodiments, as the second component 122 and the fiber matrix 140 soften, the second portion 144 moves into the second component 122 at the second transition surface 132, forming a heat bond. In some embodiments, the heat bonding leaves at least some of the plurality of fibers in the second portion 144 of the fiber matrix 140 distinctly identifiable within the second component 122 for a stronger bond than if all of the fibers of the second portion 144 were uniformly incorporated into the second component 122.

FIG. 2C (and FIGS. 3C and 4 described below) is a schematic representation of the fiber matrix 140, with the fiber matrix 140 shown as horizontal blocks with well-defined, parallel edges. However, it is understood that the edges in some embodiments may not necessarily be well-defined, or parallel, and may be curved, uneven, and or not well-defined.

In some embodiments, by employing a fiber matrix, the joint structure describe above in reference to FIGS. 2A-2C may connect two components made of different materials that are not readily bondable to each other. In addition, the processing steps in some embodiments may be generally simple and fast (e.g. heat bonding takes only seconds). Further, because no special surface treatment or adhesion promoters may be required, the joint structure may not be susceptible to the same surface deterioration that requires certain processing steps to be completed in a short span of time.

In some embodiments as described above in reference to FIGS. 2A-2C, the first material may be, for example, a silicone polymer, and the second material may be a polyurethane polymer. In other embodiments, the first material may be silicone polymer, and the second material may be a polyether ether ketone.

Figure 3A:
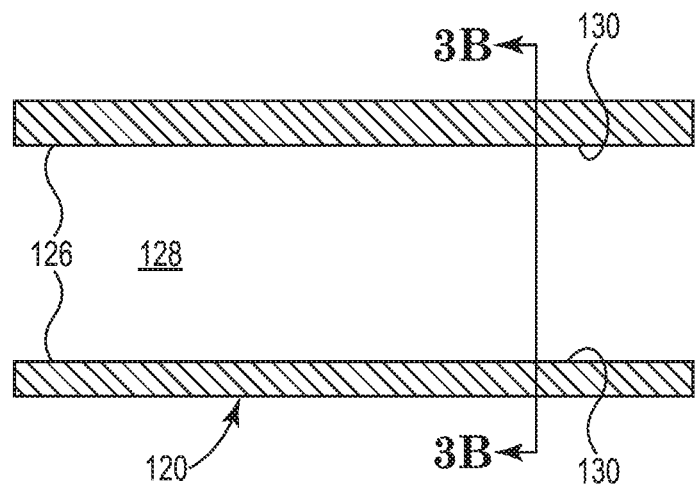
FIGS. 3A-3C are schematic views of a component of the implantable medical device shown in FIGS. 2A-2C.
Figure 3B:
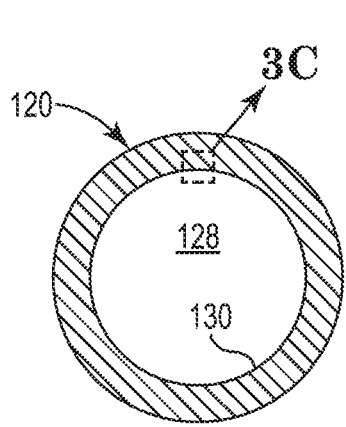
Figure 3C:
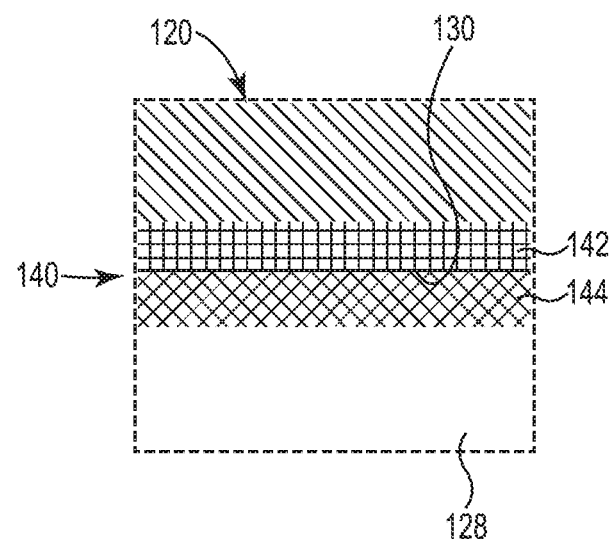

FIGS. 3A-3C are schematic views of the first component 120 of the implantable medical device shown in FIG. 1, prior to joining to the second component 122 at lead body transition 124, as shown in FIGS. 2A-2C, according to some embodiments. FIGS. 3A and 3B are, respectively, longitudinal and axial cross-sectional views of a portion of the first component 120. FIG. 3B shows a schematic cross-sectional view of the first component 120 shown in FIG. 3A. FIGS. 3A and 3B show the first component 120 including the first transition surface 130 and the first lumen 128.

FIG. 3C is a schematic enhanced cross-sectional view of a portion of the first transition surface 130 prior to being connected to second component 122. FIG. 3C illustrates the fiber matrix 140, including the first portion 142 and a second portion 144. According to some embodiments, as shown in FIG. 3C, the first portion 142 may be connected to the first component 120, while the second portion 144 may project from the first transition surface 130 and into the first lumen 128. The first portion 142 may be interpenetrated with the first component 120 as described above in reference to FIG. 2C.

In some embodiments, the fiber matrix 140 may be formed by electro-spinning or electrospraying a plurality of fibers onto an outer surface of a substrate, such as a core pin or an extrusion mandrel. The core pin or extrusion mandrel may be rotated while the fibers are electro-spun onto the outer surface. In some embodiments, the fiber matrix 140 may be formed by a plurality of randomly aligned electro-spun or electrosprayed fibers. In some embodiments, fibers may have diameters in the range of about 0.1 micrometers to 2 micrometers, for example. The fiber diameter size may be measured by taking the average size of the fibers. In some embodiments, a spacing between fibers of the fiber matrix 140 may create pores having an average pore diameter. In some embodiments, the fiber matrix 140 has an average pore diameter of at least 0.1 micrometers.

In some embodiments, at least some of the plurality of fibers may consist of a single fiber extending a plurality of times between the first component 120 and the second component 122. Such a structure may produce loops of fibers in the fiber matrix 140 that may anchor the first portion 142 in the first component 120, possibly providing a stronger joint structure.

In some embodiments, the fiber matrix 140 may form a cylinder covering the entirety of the first transition surface 130. In other embodiments, the fiber matrix 140 may cover only a portion of the first transition surface 130. In such embodiments, the fiber matrix 140 may be in the form of a series of rings, and/or a spiral extending much of the length of the lead body transition 124, and/or other forms.

According to some embodiments, interpenetration of the fiber matrix 140 and the first material may be done while the first material is in a liquid state, for example, before it has solidified by cross-linking. In some embodiments, the fibers forming the fiber matrix 140 may be electro-spun directly into the first material. In other embodiments, the fiber matrix 140 may be formed on a core pin or mandrel as described above, and then the first material in a liquid state is molded or extruded over the fiber matrix 140. The first material may then be solidified to form the first component 120 with the first portion 142 of the fiber matrix 140 interpenetrated with the first material, mechanically fixing fiber matrix 140 within the first component 120.

In some embodiments, after the first material is solidified and the first component 120 is formed, the core pin or extrusion mandrel may be removed. Removing the core pin or extrusion mandrel forms the first lumen 128. The fiber matrix 140 can transfer with the first component 120 because the fiber matrix 140 is interpenetrated with, and mechanically fixed to, first component 120. In other words, the fiber matrix 140 does not remain on the core pin or extrusion mandrel after removal of the core pin or extrusion mandrel.

Figure 4:
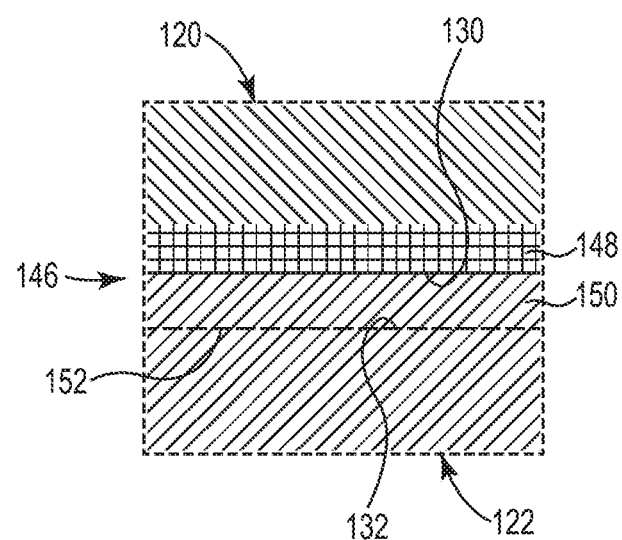
FIG. 4 is a schematic view of an alternative embodiment of a portion of the implantable medical device shown in FIG. 1.

FIG. 4 is a schematic cross-sectional view of an alternative embodiment of a joint structure connecting the first component 120 of the medical electrical lead 110, to the second component 122. FIG. 4 shows a portion of the joint structure including a fiber matrix 138 joining the first component 120 to the second component 122. The fiber matrix 138 is identical to the fiber matrix 132 described above in reference to FIGS. 3A-3C, except that it may be formed of a material that does not bond readily to either the first material or the second material.

According to the embodiment shown in FIG. 4, the fiber matrix 148 may include a first portion 148 and a second portion 150. The first portion 148 may be connected to the first component 120, as with first portion 140 described above in reference to FIGS. 3A-3C. Because the first portion 148 of the fiber matrix 146 may be mechanically fixed to the first component 120, the fiber matrix 146 may be made of a material that does not bond readily to the first material of the first component 120. In contrast to the embodiment described above in reference to FIGS. 2A-2C, in the embodiment shown in FIG. 4, the second portion 150 may be interpenetrated with the second material. In some embodiments a solution 152 of the second material in a solvent may be interpenetrated with the second portion 150. In some embodiments, the solvent does not dissolve either the first material of the first component 120 or the fiber matrix 146. Once the solvent is evaporated, leaving behind the second material, the second portion 150 may be mechanically fixed to the second material. The second material of second component 122 may be easily bonded to the interpenetrated second material from solution 152 by, for example, heat bonding, such that the interpenetrated second material becomes part of the second component 122. In some embodiments, once the interpenetrated second material from solution 152 becomes part of the second component 122, the second portion 150 may directly contact the second component 122, as there is no need for a third material between the second portion 150 and the second component 122. Because the second portion 150 of the fiber matrix 146 may be mechanically fixed to the second component 122, the fiber matrix 146 may be made of a material that does not bond readily to the second material.

In some embodiments as described above in reference to FIG. 4, the first material may be a silicone polymer, the second material may be a polyurethane polymer, and the fiber matrix 146 may be an aliphatic polyamide polymer. The solvent may include tetrahydrofuran. In other embodiments, the fiber matrix 146 may be a fluoropolymer, such as poly(vinylidene fluoride-co-hexafluoropropene) (PVDF-HFP), or styrene-isobutylene-styrene (SIBS).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for joining a first component and a second component of an implantable medical device, the method comprising:
   interpenetrating a first portion of a fiber matrix, including a plurality of electro-spun or electrosprayed fibers, within a first material, the first material being a silicone polymer in a liquid state;
   forming the first component by solidifying the first material, wherein the first portion of the fiber matrix is mechanically fixed within the silicone polymer of the first component and a second portion of the fiber matrix projects from the first component; and
   connecting the second portion of the fiber matrix to the second component to join the first component to the second component.

2. The method of claim 1, wherein connecting the second portion of the fiber matrix to the second component includes:
   interpenetrating the second portion of the fiber matrix within a liquid solution including a first portion of the second material;
   solidifying the first portion of the second material by evaporating a solvent from the liquid solution such that the second portion of the fiber matrix is mechanically fixed within the first portion of the second component; and
   forming the second component by heat bonding a second portion of the second component to the first portion of the second component such that at least a portion of the second portion of the fiber matrix is distinctly identifiable within the second component.

3. The method of claim 2, wherein the second material is a polyurethane polymer, and the fiber matrix is an aliphatic polyamide polymer.

4. The method of claim 1, wherein interpenetrating the first portion of the fiber matrix within the first material includes electro-spinning a fiber directly into the first material.

5. The method of claim 1, wherein interpenetrating the first portion of the fiber matrix within the first material includes:
   electro-spinning at least one fiber onto a substrate to form the fiber matrix; and
   overmolding the first material onto the fiber matrix on the substrate.

6. The method of claim 1, wherein solidifying the first material is by cross-linking portions of the first material around portions of the first portion of the fiber matrix.

7. The method of claim 1, wherein connecting the second portion of the fiber matrix to the second component includes heat bonding the second portion of the fiber matrix to the second component.

8. The method of claim 1, the second material is a polyurethane polymer, and the fiber matrix is poly(vinylidene fluoride-co-hexafluoropropene) polymer.

9. The method of claim 1, wherein the second material is a polyurethane polymer, and the fiber matrix is styrene-isobutylene-styrene polymer.

10. A method for joining a first component, including a silicone polymer, and a second component, including a polyurethane polymer, of an implantable medical device, the method comprising:

electro-spinning a first portion of a plurality of fibers directly into a the silicone polymer, the silicone polymer being in a liquid state;
   solidifying the silicone polymer to form the first component, wherein the first portion of the plurality of fibers is mechanically fixed within the first component and a second portion of the plurality of fibers projects from the first component; and
   connecting the second portion of the plurality of fibers to the second component to join the first component to the second component.

11. The method of claim 10, wherein connecting the second portion of the plurality of fibers to the second component includes:

interpenetrating the second portion of the plurality of fibers within a liquid solution of the second material; and
   solidifying the second material to form the second component by evaporating a solvent from the liquid solution such that the second portion of the plurality of fibers is mechanically fixed within the second component.

12. The method of claim 11, wherein the solidified second material is a first portion of the second component, the method further comprising heat bonding second portion of the second component to the first portion of the second component.

13. The method of claim 12, wherein at least a portion of the second portion of the plurality of fibers is distinctly identifiable within the first portion of the second component.

14. The method of claim 10, wherein at least some fibers of the plurality of fibers consist of a single fiber extending a plurality of times between the first component and the second component, the fibers forming loops within the first component.

15. The method of claim 10, wherein solidifying the first material is by cross-linking portions of the first material around portions of the first portion of the plurality of fibers.

16. The method of claim 10, wherein connecting the second portion of the plurality of fibers to the second component includes heat bonding the second portion of the plurality of fibers to the second component.

17. The method of claim 10, wherein the plurality of fibers is an aliphatic polyamide polymer.

18. The method of claim 10, wherein and the plurality of fibers is poly (vinylidene fluoride-co-hexafluoropropene) polymer.

19. The method of claim 10, wherein the plurality of fibers is styrene-isobutylene-styrene polymer.

20. The method of claim 10, wherein at least some fibers of the plurality of fibers form pores between the fibers.

\* \* \* \* \*